United States Patent
Calasso et al.

(10) Patent No.: US 8,000,762 B2
(45) Date of Patent: Aug. 16, 2011

(54) BODY FLUID SAMPLING DEVICE

(75) Inventors: Irio G. Calasso, Arth (CH); Patrick Griss, Otelfingen (CH); Emad Sarofim, Hagendorn (CH); Rainer Jaeggi, Thalwil (CH); Uwe Kraemer, Ilvesheim (DE); David Hasker, San Jose, CA (US); Volker Zimmer, Morbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 911 days.

(21) Appl. No.: 11/469,123

(22) Filed: Aug. 31, 2006

(65) Prior Publication Data

US 2006/0293611 A1    Dec. 28, 2006

Related U.S. Application Data

(63) Continuation of application No. PCT/EP2005/002316, filed on Mar. 4, 2005.

(30) Foreign Application Priority Data

Mar. 6, 2004  (EP) .................................... 04005385

(51) Int. Cl.
 *A61B 5/04* (2006.01)
(52) U.S. Cl. ......................... 600/345; 600/347; 600/365
(58) Field of Classification Search .......... 600/325–327, 600/345, 347, 348, 354, 573, 575, 576, 577, 600/578, 583–584
See application file for complete search history.

(56) References Cited

U.S. PATENT DOCUMENTS

| | | | |
|---|---|---|---|
| 4,218,421 A | | 8/1980 | Mack, Jr. et al. |
| 5,108,889 A | * | 4/1992 | Smith et al. ....................... 435/4 |
| 5,163,442 A | * | 11/1992 | Ono .............................. 600/573 |
| 5,318,514 A | | 6/1994 | Lange et al. |
| 5,582,184 A | * | 12/1996 | Erickson et al. .............. 600/576 |
| 5,762,770 A | * | 6/1998 | Pritchard et al. ......... 204/403.14 |
| 5,801,057 A | | 9/1998 | Smart et al. |
| RE36,268 E | | 8/1999 | Szuminsky et al. |
| 6,063,040 A | * | 5/2000 | Owen et al. ................... 600/573 |

(Continued)

FOREIGN PATENT DOCUMENTS

CN    1407327 A    4/2003

(Continued)

OTHER PUBLICATIONS

Final Office Action received in related U.S. Appl. No. 11/470,368, mailed Jun. 11, 2009.

(Continued)

*Primary Examiner* — Patricia C Mallari
*Assistant Examiner* — Michael D'Angelo
(74) *Attorney, Agent, or Firm* — Woodard, Emhardt, Moriarty, McNett & Henry LLP (57) ABSTRACT

Body fluid sampling device comprising a sampling element having a fluid pathway (11) for receiving body fluid, at least a portion of the fluid pathway is open to the environment and further comprising a fluid receiving means (40) being spaced from the fluid pathway so that fluid in the pathway will not contact the fluid receiving means initially. The fluid receiving means has two or more test zones (45) for performing analytical reactions. Fluid from the channel is contacted with the fluid receiving means either by bringing the fluid receiving means and the fluid into mechanical contact or by electrically transporting fluid from the channel onto the fluid receiving means.

33 Claims, 8 Drawing Sheets

U.S. PATENT DOCUMENTS

| | | | |
|---|---|---|---|
| 6,132,449 A * | 10/2000 | Lum et al. | 606/181 |
| 6,364,890 B1 | 4/2002 | Lum et al. | |
| 6,375,626 B1 | 4/2002 | Allen et al. | |
| 6,589,260 B1 | 7/2003 | Schmelzeisen-Redeker et al. | |
| 6,612,111 B1 | 9/2003 | Hodges et al. | |
| 6,660,018 B2 | 12/2003 | Lum et al. | |
| 6,821,483 B2 | 11/2004 | McGarraugh et al. | |
| 6,988,996 B2 * | 1/2006 | Roe et al. | 600/584 |
| 7,005,857 B2 * | 2/2006 | Stiene et al. | 324/449 |
| 2002/0043463 A1 | 4/2002 | Shenderov | |
| 2002/0114715 A1 | 8/2002 | Yoon et al. | |
| 2002/0168290 A1 | 11/2002 | Yuzhakov et al. | |
| 2003/0018282 A1 | 1/2003 | Effenhauser et al. | |
| 2003/0028125 A1 * | 2/2003 | Yuzhakov et al. | 600/583 |
| 2003/0059350 A1 | 3/2003 | Sacherer | |
| 2003/0073931 A1 * | 4/2003 | Boecker et al. | 600/573 |
| 2003/0083685 A1 | 5/2003 | Freeman et al. | |
| 2003/0135333 A1 | 7/2003 | Aceti et al. | |
| 2003/0205632 A1 * | 11/2003 | Kim et al. | 239/690 |
| 2003/0212344 A1 | 11/2003 | Yuzhakov et al. | |
| 2004/0022681 A1 | 2/2004 | Hantschel et al. | |
| 2004/0064068 A1 | 4/2004 | DeNuzzio et al. | |
| 2004/0176732 A1 | 9/2004 | Frazier et al. | |
| 2004/0193072 A1 * | 9/2004 | Allen | 600/583 |
| 2004/0260204 A1 | 12/2004 | Boecker et al. | |
| 2005/0043597 A1 | 2/2005 | Xie | |
| 2005/0149088 A1 | 7/2005 | Fukuda et al. | |
| 2005/0234368 A1 | 10/2005 | Wong et al. | |
| 2006/0087064 A1 | 4/2006 | Daniel et al. | |
| 2006/0100654 A1 | 5/2006 | Fukuda et al. | |
| 2006/0276724 A1 | 12/2006 | Freeman et al. | |
| 2007/0016103 A1 | 1/2007 | Calasso et al. | |
| 2007/0038149 A1 | 2/2007 | Calasso et al. | |
| 2007/0126536 A1 | 6/2007 | Fork et al. | |
| 2007/0250099 A1 | 10/2007 | Flora et al. | |
| 2008/0268669 A1 | 10/2008 | Van Schuylenbergh et al. | |

FOREIGN PATENT DOCUMENTS

| | | | |
|---|---|---|---|
| CN | 1431884 A | | 7/2003 |
| EP | 0199484 B1 | | 10/1986 |
| EP | 0458405 A1 | | 11/1991 |
| EP | 0299517 B1 | | 6/1993 |
| EP | 0565970 B1 | | 6/1994 |
| EP | 0723418 B1 | | 7/1996 |
| EP | 1 360 933 | | 11/2000 |
| EP | 1 101 443 A2 | | 5/2001 |
| EP | 1 360 931 A1 | | 11/2003 |
| EP | 1371419 A1 * | | 12/2003 |
| EP | 1424040 A1 | | 6/2004 |
| EP | 1 508 304 | | 10/2006 |
| EP | 1 360 934 | | 12/2006 |
| GB | 1 418 337 | | 12/1975 |
| WO | WO 97/18036 | | 5/1997 |
| WO | WO97/42888 A1 | | 11/1997 |
| WO | WO 01/66010 A1 | | 9/2001 |
| WO | WO 01/72220 A1 | | 10/2001 |
| WO | WO 02/07503 A1 | | 1/2002 |
| WO | W002/50534 A1 | | 6/2002 |
| WO | WO 02/49507 A1 | | 6/2002 |
| WO | WO 02/062210 A1 | | 8/2002 |
| WO | W002/100253 A2 | | 12/2002 |
| WO | W02005/084530 A2 | | 9/2005 |
| WO | W02005/084545 A1 | | 9/2005 |
| WO | W02005/084546 A3 | | 9/2005 |

OTHER PUBLICATIONS

Non-Final Office Action received in related U.S. Appl. No. 11/470,021, mailed Feb. 27, 2009.

Non-Final Office Action received in related U.S. Appl. No. 11/470,368, mailed Nov. 14, 2008.

Final Office Action received in related U.S. Appl. No. 11/470,021, mailed Sep. 8, 2009.

Non-Final Office Action received in related U.S. Appl. No. 11/470,368, mailed Dec. 24, 2009.

English translation-in-part of Japanese Unexamined Patent Publication No. 150458/1991.

U.S. Appl. No. 11/470,021 to Calasso et al., Non-Final Office Action mailed Oct. 21, 2010.

* cited by examiner

BODY FLUID SAMPLING DEVICE

REFERENCE TO RELATED APPLICATIONS

This application is a continuation of International Application No. PCT/EP2005/002316 filed Mar. 4, 2005, published on Sep. 15, 2005 as WO 2005/084545 A1, which is incorporated by reference in its entirety.

BACKGROUND

The present invention relates to the field of body fluid analyses in order to make a diagnosis or to monitor the concentration of multiple analytes such as the blood glucose, lactate, cholesterol, lipids etc.

The invention concerns a device and system for sampling small amounts of sample fluid. A body fluid testing device comprises a sampling element with a fluid pathway for receiving sample fluid therein. At least a portion of the fluid pathway is open to the environment. The testing device further comprises a fluid receiving means which is separated from the fluid pathway so that fluid in the pathway will not contact the fluid receiving means in a first state. The device or system can be brought into a second state in which at least a portion of the pathway contacts the fluid receiving means so that fluid is transferred. The fluid receiving means comprises two or more test zones each adapted to the detection of a particular analyte. Based on signals from a sensor of the fluid receiving means analyte concentrations can be determined.

Systems for sampling body fluids are already known in the prior art in which body fluid is taken up into a disposable element. Blood collection and analytical systems are e.g. known from the document EP 0 199 484 which comprise a disposable unit with a capillary to collect body fluid and to transport the body fluid into a detection area. The further development of this concept is described in WO 97/42888. The arrangement described in this patent is particularly suitable for collecting relatively small amounts of body fluids which is primarily accomplished by pressing a ring onto the area surrounding a collection site and a pump movement. A system for analysis based on small amounts of interstitial fluid is known from EP 0 723 418. For this purpose a very thin closed hollow needle is inserted into the dermis and interstitial fluid is conveyed through the needle to a test zone by applying pressure to the area surrounding the puncture site. A highly miniaturized arrangement which also utilizes a closed needle to withdraw body fluid is known from U.S. Pat. No. 5,801,057. A particular advantage of this arrangement is the extremely thin needle which can be inserted into the arm region of a patient without essentially any pain.

Whereas the arrangement described in U.S. Pat. No. 5,801,057 already fulfils numerous practical requirements, some features are in need of improvement. A general problem with the sampling devices according to the previously mentioned document is to manufacture the hollow needle cost-effectively and as small as possible.

With this aim body fluid samplers which have an open fluid pathway structure are contemplated. The documents US 2003/0018282 and US 2003/0028125 both describe skin piercing devices which have an open channel for body fluid sampling which at least partially is located in a region of a piercing needle. Body fluid sampled into the fluid pathway is transferred to a testing zone which is fixed to the skin piercing element. In particular US 2003/0028125 describes that the skin piercing element is integral with a part of a test strip. A further document that contemplates a similar sampling and testing device with provision of a pooling area is described in US 2002/0168290.

SUMMARY

The prior art sampling and testing devices describe embodiments where sample from a capillary channel is directly transferred to a testing zone which is in contact with the channel. Contrary to that the present invention proposes body fluid sampling and testing devices where the fluid pathway in a phase in which sample is taken up is out of fluidic contact with a testing zone. After having taken up a fluid sample into the fluid pathway at least a portion of the fluid pathway is being contacted with a fluid receiving means that receives fluid from the pathway. The fluid receiving means itself may comprise two or more test zones or it may be a zone that transports sample to two or more test zones. Wetting of the test zones therefore can be initiated in a controlled manner by the contacting step. This triggering of test zone wetting has the advantage that the reaction time (i.e. the time between contacting a test chemistry with sample fluid and reading of test results) can be controlled which leads to higher accuracy of analyte determination. A further advantage compared to the prior art sampling devices is that fluid sampling and contacting of the sampling element with a testing zone can be conducted at different locations. Fluid sampling for example can be done at the front end of a hand-held apparatus while contacting with a testing zone can be made within the apparatus. Due to this shuttle function of the sampling element optics or other evaluation means can be moved into the interior of a housing which is advantageous with view to the limited space at the front end. A further advantage of contacting the test zone or the fluid receiving means with sample already present in the fluid pathway is that contact can be made with a portion of the fluid pathway that does not contain the first fluid emerging the body. By this, influences of plasma and substances from the body surface can be avoided or reduced.

Furthermore when the sampling element is a skin piercing element a physical separation of the test zones from blood during the sampling step avoids that test chemistry diffuses into the human body.

The present invention which employs a fluid receiving means comprising two or more test zones further provides the advantage that more than one analytical test can be made after having made one sampling step. Due to the order of operations, i.e. the filling of a capillary and contacting this capillary with the two or more test zones it can be ascertained that the test zones are provided with sample fluid in virtually the same manner. This is advantageous over embodiments where sample is received at one end of a cascade of test zones since in this prior art embodiment the sample fluid is changed by the previous test zones before reaching a successive test zone. Further undesired filtering and diffusion processes may occur.

Further two or more fluid receiving means each holding one or more test zones can be contacted with the same sampling element. Contacting of the fluid receiving means with the sampling element can be e.g. made simultaneously or subsequently.

One particular field of application of systems and devices for withdrawing small amounts of body fluid is the so-called spot-monitoring in which the concentration of particular analytes present in body fluids is determined at a particular time.

Such measurements can be carried out repeatedly at time intervals in order to monitor a change of analyte concentration.

The present invention is particularly advantageous for performing so-called panel tests where simultaneously multiple tests are performed. Such panel tests are e.g. known to test lipids, cardiac parameters, liver parameters or other combinations of parameters to determine basic blood constituents as e.g. glucose, lactate, cholesterole, triglycerides, urea, uric acid, creatinine. Further immunological tests can be performed where an analyte in the sample fluid interacts with an antibody. Various detection systems are known for such immunological tests which e.g. involve coloured markers allowing to detect if an analyte is present or to measure its concentration.

Test zones are provided on the fluid receiving means which are adapted to perform analytical testing for a specific parameter. Adaption means that the test zones comprise a test chemistry which allows specific detection of a particular parameter.

Alternatively to having two or more test zones for different analytes on a fluid receiving means, two or more zones for the same analyte can be provided, e.g. for statistical reasons or the zones can be optimized for different analyte concentrations.

The present invention enables the process of analytical testing to be greatly simplified.

Simplification is reached by employing a sampling element which receives body fluid in a fluid pathway and this fluid then can be automatically contacted with a fluid receiving means including a test zone. A simplification of testing not only is advantageous for current users, it hopefully also has the effect that more people will do testing of blood or urine parameters on a regular basis.

A sampling device and system according to the present invention serves to withdraw small amounts of body fluid. In this context body fluids are understood in particular as blood, interstitial fluid and mixtures of these body fluids. Whereas in conventional blood collection systems this is usually carried out on the finger pad, the collection system according to the invention can also be used to withdraw blood from alternate sites on the body such as the forearm and the palm. In a preferred embodiment the sampling element is a skin piercing element. A skin piercing element for withdrawing small amounts of body fluid according to the present invention has a protruding portion with a sharpened end for piercing skin. Within at least a region of the protruding portion a fluid pathway is located which has a capillary activity to transport body fluid. At least a part of the capillary structure, preferably the whole capillary, is open to the outside along its extension. A capillary structure is understood within the scope of the invention as a body which transports body fluid as a result of capillary forces towards the proximal end of the capillary structure when the distal area is contacted with body fluid. With regard to this function the capillary structure according to the invention is similar to the open needle structures described in US 2003/0018282 and US 2003/0028125 to which reference is made herewith. However, an important difference is that these documents describe microneedles where the capillary channel is steadily in fluidic contact with a test zone so that body fluid received in the capillary channel is directly applied to the test zone and hence initiates reaction.

The longitudinal extension of the skin piercing element extends from a proximal end which provides a holding area to a distal end having a protruding portion which is intended to be inserted into the skin. The hollow needles of the prior art have an opening at their distal end through which body fluid can enter and the fluid pathway then changes into a closed channel or chamber in which the test zone is located. In contrast the capillary structure according to the present invention preferably is open to the outside over its entire longitudinal extension and the fluid path is not closed by a test zone.

Open capillaries can be manufactured by photolithographic methods like those described in the document U.S. Pat. No. 5,801,057 and which are known from the field of semiconductor technology. It is also possible to provide channels, grooves etc. which are open to the outside in solid needles by milling, etching and such like. The capillaries can also be formed in plastics during manufacturing as e.g. micro injection molding. Depressions which provide the capillary channel may lead from the tip or at least from a region adjoining the sampling tip respectively the skin piercing element to a proximal holding region which is connectable to a holding device. The depressions or capillaries do not necessarily have to run in straight lines, but can also for example be arranged in spirals, meanders etc. Furthermore the capillaries may be arranged in a network with bifurcations, split capillaries, etc.

In accordance with the present invention where the fluid receiving means comprises two or more test zones it is preferred when the capillary splits into smaller channels so that the sample fluid is laterally extended. In such cases contacting of the two or more test zones then can be best done by contacting different sub-channels with the different test zones.

In a further embodiment two or more fluid receiving means each having one or more test zones can be contacted with the same sampling element.

The cross-section of the capillaries can for example be V-shaped, semi-circular or also rectangular.

Such channels are preferably generated by etching processes as photochemical milling (PCM). PCM is the machining of metal structures without heating or mechanically milling the starting material. PCM is based on optical pattern transfer and etch processes. It is known to be a micromachining technology.

The starting materials are metal sheets. There is a wide range of different materials to choose from, ranging from medical steel to aluminium and invar. In the case of steel, most of the standard medical types are available. When compared to silicon, glass or quartz, the cost of the raw material steel is much lower.

PCM is a Photolithography based fabrication method, i.e. the outline of a structure to be machined is transferred optically. A photosensible polymer is applied onto the metal sheet in a film. The polymer is referred to as photoresist and comes in two types:
1. Dry resist (foil laminated onto the substrate)
2. Wet resist (liquid spread and cured on the substrate)

Upon selective illumination of the photoresist via a shadow mask, the photoresist can be selectively removed from the substrate (which is often referred to as patterning).

When the patterned substrate is exposed to aqueous solution (e.g. Iron (III) chloride for steel) which reacts with the substrate material, the material is selectively removed from the areas where there is no photoresist left (referred to as the "etch"). There are two main principles of how the substrate can be brought in contact with the substrate.
1. dipping of the substrate into a bath of etchant
2. spraying of the etchant on the substrate The etch step is in its nature generally isotropic, i.e. the etch rate is approximately the same in all directions. Isotropicity can be influenced by a large number of parameters during the photolithography and during the etch, thus it is possible to control the etch profile within certain limits.

Spray etching offers larger flexibility in controlling etch rates and profiles when compared to dip etching.

In most cases, it is imperative that the photoresist layer is removed from the substrate to obtain the sampling devices. Removal of photoresist layer is normally a wet process.

In addition to the already mentioned methods for incorporating capillary channels into surfaces, it is also possible to generate the capillary channels by assembling bodies in a way that capillary gaps are created. Thus it is for example possible to fasten two or more solid needles together for example by welding such that the contact areas of the solid needles form capillary channels. In a corresponding manner it is also possible to twist wires together in the form of a stranded wire such that numerous contact areas are formed which generate the capillary channels. Further skin-piercing elements with fluid pathways can be created by applying one or more layer of materials (e.g. laminated foils) onto a flat needle in a way that a capillary gap is created between the layers or is provided in one such layer.

The capillary channels which provide the fluid pathway typically have a greater depth than width. The ratio of depth to width (generally referred to as aspect ratio) is preferably 0.3 to 3. The cross-section of the capillary channel is typically larger than 2500 $\mu m^2$ and less than 1 $mm^2$. Preferably the capillary channel has a width in the range of 50 to 450 micrometers, most preferred around 200 micrometers. As already stated above it is advantageous that the capillary channels are open to the outside such that they can take up body fluid while the capillary structure is inserted into the body. In order to achieve a good uptake of body fluid the area of the capillary structure that is open to the outside should have a length of 0.5 mm or more.

The shape of a skin piercing element is relatively uncritical. It can for example be in the form of a small cube. Special measures are usually not necessary to mount the skin piercing element in a drive unit but a holding region located at the proximal end of the skin piercing element is preferred. Advantageously the holding area is formed integral with the other regions of the skin piercing element. Piercing element designs can be employed that are known for disposable lancets of conventional blood sampling systems. For example the holding region can have tapers into which spring elements of a holder of a drive unit engage in order to hold the piercing element. The piercing element is advantageously positioned within a holder in such a manner (for example by pressing the end of the piercing element facing away from the tip against a stop) that it allows a good control of the piercing depth. Reference is made to the document EP B 0 565 970 with regard to such a holder and the interaction between the holder and the disposable lancing unit.

The body fluid testing device in addition to the sampling element has a fluid receiving means which is spatially separated from the fluid pathway of the sampling element so that fluid in that pathway will not contact the fluid receiving means during filling. The fluid receiving means and the pathway, however, are contacted to each other after fluid sample has been received in at least a part of the fluid pathway and when start of the analytical reaction is desired.

The spatial separation of sampling element and fluid receiving means enables embodiments where the sampling element is employed as a shuttle to transport sampled fluid to a fluid receiving means. This is particularly advantageous when fluid sampling is made in a spatially restricted area (e.g. the front end of apparatus) and the fluid receiving means does not fit well into this limited space. The latter in particular is the case for fluid receiving means fixed to a tape as e.g. described in European patent application 0 202 6242.4, U.S. Pat. No. 4,218,421 and EP 0 299 517. The shuttle function enables a testing process with the steps of sampling body fluid into the sampling element transporting sampled body fluid with the sampling element to a fluid receiving means contacting the fluid receiving means with body fluid on the sampling element, detecting a change of the fluid receiving means which relates to the concentration of two or more analytes.

When a magazine with fluid receiving means is employed there further can be the steps of exposing a specific fluid receiving means from the stored fluid receiving means to contact the sampling element loaded with sample fluid. When the specific fluid receiving means has been evaluated a further fluid receiving means can be exposed to contact sample fluid on sampling element.

A system according to above shuttle concept therefore has one or more sampling elements and a transport means to transport the sampling element into contact with a fluid receiving means. The sampling element may be a skin piercing element and the system then has a suitable driver. The drive for piercing and the transport means may be employed in the same drive unit. Further the system may comprise a storage unit for multiple fluid receiving means. The system further may comprise an exposing unit for successively exposing fluid receiving means to receive fluid.

The fluid receiving means is a structure that can take up fluid from a fluid pathway of the sampling element. This uptake of fluid e.g. can be accomplished by an electrical potential applied between fluid in the fluid pathway and the fluid receiving means. Preferably, however, the fluid receiving means has a higher capillarity than the fluid pathway of the skin piercing element so that during contact fluid is automatically taken up. In this regard the fluid receiving means can be made from a fleece or fabric material that has a high capillarity and is hydrophilic (at least in areas for fluid take-up). The fluid receiving means may have a particular region which comprises such material of high capillarity or the whole area of the fluid receiving means can act as receiving means for fluid from the fluid channel. The fluid receiving means may virtually only comprise two or more test zones which can be covered with a fabric or woven material or the fluid receiving means may be more complex and allows for pre-processing of sample fluid and/or transport of fluid to sensor/test zones. Pre-processing may comprise filtration of fluid sample and/or a mixing with reagents. The test zones e.g. can be spotted or printed onto a substrate to obtain a fluid receiving means with analytical capability.

The fluid receiving means comprises two or more test zones with a chemistry layer that contains reagents for detecting two or more analytes.

The reagents undergo a detectable change due to reaction with the analyte to be detected. Typical reagents for detecting glucose are based for example on glucose oxidase in conjunction with a chromogenic redox system. Reagents are well known in the prior art for optical evaluation which form a colour with glucose from the body fluid. Furthermore reagents are also known from the field of blood sugar test strips which allow electrochemical detection of analytes. The reagent mixtures that are used are usually in a solid state and, due to their constituents (e.g. aluminium oxide, kieselguhr and such like), have such a high capillarity that they can take up body fluid from the capillary channel. Since these detection systems are well-known from the prior art they are not described in more detail herein but reference is made to U.S. Pat. No. 5,762,770 and U.S. Pat. No. 36,268. Similar test systems are known for various other analytes.

When the sampling element is a skin piercing element the body fluid collection system according to the present invention additionally has a drive unit which, when activated, moves the skin piercing element from a first into a second position such that it performs a lancing movement. Suitable drive units are well-known from the field of blood sampling systems. It can for example contain a spring which is cocked by the user and when released drives the skin piercing element. A particularly advantageous drive unit is described in EP B 0 565 970.

Systems for body fluid analysis comprise a detection unit. If a sensor/test zone containing reagent is used which changes colour or forms a colour when an analyte is present, the system can have an optical detection unit comprising a light source and a detector to detect transmitted or reflected light.

According to the present invention the fluid receiving means has two or more test zones. These can be evaluated by the same optics in a way that the fluid receiving means and the optics are moved to one another so that the test zones are successively read. Further it is possible to employ optics with multiple detection channels so that the two or more test zones can be evaluated simultaneously.

When electrochemical detection is employed, the system has electrodes which contact the test zone or the fluid receiving means. For evaluation of raw signals the system can have electronic devices known in the prior art in order to determine the concentration of analyte for example by measuring the so-called Cotrell current (see e.g. U.S. Pat. No. 36,268). Other detection principles may also be employed as well as a combination of different detection principles for evaluation of the test zones.

With the skin piercing element according to the present invention body fluid can be withdrawn while the protruding portion is inserted into the skin (i.e. withdrawal of sample directly from the body and/or from body fluid emerging on the body surface) or the protruding portion can be retracted from the body after piercing and takes up body fluid that emerges on the body surface. A partial withdrawal in which the protruding portion remains in the body but the lancing channel in the skin is opened to collect body fluid is especially suitable for sampling at the arm. This is due to the fact that small incisions on the arm close very rapidly such that no fluid or only very small amounts of fluid emerge after piercing. On the other hand the sensitivity to pain is much less pronounced on the arm as compared for example to the finger and thus when the protruding portion remains in the body this is not felt to be painful. As described above an advantage of a capillary structure that is open to the outside is that fluid can be taken up through the open fluid channel whereas the area for taking up liquids by hollow needles is limited to the front end of the needle. The latter is particularly disadvantageous when the needle opening becomes sealed by tissue (due to a stamped out tissue portion) during the piercing process such that no liquid or only an inadequate amount can be taken up.

Furthermore a withdrawal process can be carried out with the sampling device according to the invention which is a combination of the previously mentioned processes. In this combined process piercing is carried out firstly, the protruding portion is pulled back over a part of the piercing path and is allowed to reside there for a collection period of few seconds. An advantage of this process is that the retraction of the protruding portion exposes a part of the lancing channel such that body fluid collects therein and can enter from there into the fluid pathway of the skin piercing element. Further such withdrawal process has the advantage that blood on the skin surface can be taken up by the open channel. Depending on the circumstances it may even be possible to remove residual blood almost completely so that no blood is seen by the user.

A further decisive factor which is important for an efficient uptake of body fluid into the fluid pathway is the wettability of the capillary channel. When capillary structures made of silicon are used, these are usually adequately wettable due to a silicon oxide layer on the surface. If metals or plastics are used for the capillary structure, these are often relatively difficult to wet. This can be counteracted by a number of different measures such as silication of the surface. The wettability is usually adequate when the liquid in the capillaries has a concave meniscus which is the case when the wetting angle is less than 90°. The present invention will be described in more detail with regard to the figures. The description of specific embodiments as shown in the figures, however is not intended to limit the scope of the present invention.

BRIEF DESCRIPTION OF DRAWINGS

The present invention will be described in more detail with regard to the figures, in which.

DESCRIPTION OF SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

Figure 1A:
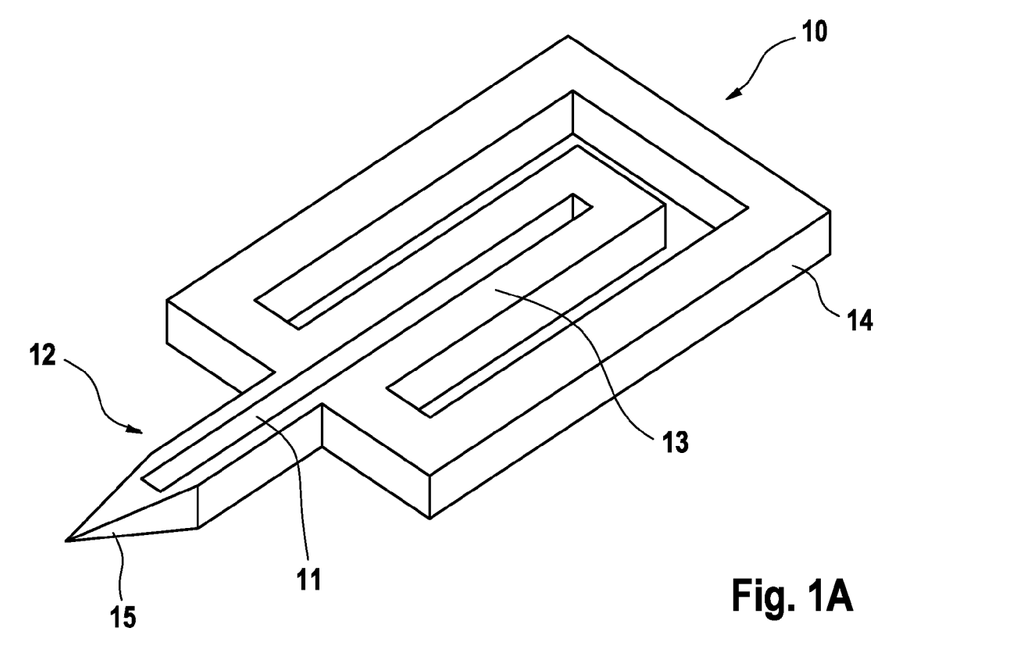
FIG. 1A schematically shows a first embodiment of the a skin piercing element with a moveable fluid pathway in a perspective view.

FIG. 1 shows a skin piercing element (10) which has a fluid pathway (11) which runs in an elongated portion (12, 13) of the skin piercing element. This portion is connected to a holder (14) in form of a frame. The elongated portion has a protruding portion (12) which protrudes from the holder portion (14). At the front end of the protruding portion a sharpened tip (15) is located. The sharpened tip (15) enables penetration of the skin surface during pricking with the skin piercing element. The fluid pathway (11) starts in the front end region of the protruding portion and extends into a movable portion (13) which is located in the holder frame (14). The fluid pathway is an open capillary channel which permits body fluid which contacts the channel in the region of the protruding portion to move into the moveable portion (13) by means of capillary action. As depicted in FIG. 1A protruding portion, moveable portion and frame portion of the skin piercing element are formed integrally. The skin piercing element (10) can be made by etching processes. As well known in silicon manufacturing processes a wafer of silicon material can be etched to provide devices comprising tips and capillary channels. For mass production it is however advantageous to produce the skin piercing elements by etching of thin metal plates. It is particularly advantageous that the sharpened tip (15) of the protruding portion (12) can be formed during the etching process as well so as to avoid separate grinding steps.

As can be seen from FIG. 1A there is no reagent or sensor contacting the fluid channel which would receive body fluid immediately after the channel has been filled with sample fluid. The present invention contrary to that proposes to locate a test zone or sensor separately on a fluid receiving means.

Figure 1B:
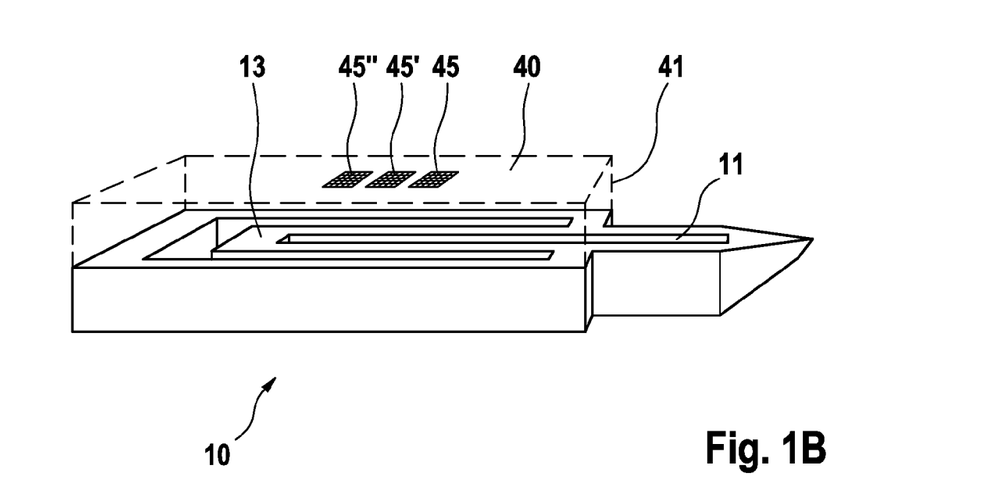
FIG. 1B shows the FIG. 1A embodiment with a fluid receiving means including a test zone in a perspective view.

FIG. 1B shows the skin piercing element (10) of FIG. 1A together with a fluid receiving means including a test zone. The fluid receiving means (40) is shown schematically. The fluid receiving means (40) is located on the upper side of the skin piercing element on which side the fluid channel (11) is open to the environment. The fluid receiving means (40) is, however, initially spaced from the fluid pathway (11) so that sample fluid within the fluid pathway does not contact the fluid receiving means. Therefore no fluid transfer from the fluid pathway onto the fluid receiving means occurs in this geometry of the fluid sampling device. In the depicted embodiment the fluid receiving means essentially consists of a holding structure (41) which provides proper orientation and spacing of the fluid receiving means relative to the skin piercing element and three test zones (45, 45', 45"). In the depicted embodiment the test zones comprise different reagent chemistries which produce optical signals based on the concentration of three analytes in the body fluid. Due to the incorporation of porous materials as e.g. kieselghur or titanium dioxid the reagent chemistry already has high capillarity that sucks fluid from capillary channel (11). The reagent chemistries are applied to a carrier surface. As shown in FIG. 1B initially the fluid pathway and the test zones (45, 45', 45") are spaced apart so that body fluid located in the capillary channel (11) will not be transferred to the test zones (45, 45', 45"). After fluid has been received in the fluid pathway and has filled the moveable section (13) the body fluid sampling device is primed for measurement. By means of mechanical actuation the moveable section (13) can be bend in direction of the test zones so that body fluid located in the fluid pathway contacts the test zones and wets the reagent chemistries. This mode of contacting the test zones with sample fluid has several advantages over the prior art devices.

A first advantage over the prior art is that measurement can be initiated at a specific point in time. This means that the time between wetting of the test zones and measurement of the final signal can be chosen at will. The time period, however, is shorter than the drying time of blood in the capillary. Knowing or controlling the time of reaction improves accuracy of the measurement. Further a signal can be measured beginning directly after wetting which allows to monitor reaction kinetics. Evaluation of this early signals can be used to improve accuracy of the measurement result as well. A further advantage can be seen from FIG. 1B. When the moveable section (13) is contacted with the test zones (45, 45', 45") it contacts an intermediate section of the fluid channel (11) but not the very end. Fluid contaminated by the skin surface or containing interstitial fluid (ISF) enters the capillary first and therefore resides after filling in the end portion of the capillary. Fluid in this end portion is not contacted with the fluid receiving means, therefore the end portion is called discharge region. The intermediate portion of the channel therefore contains fluid almost uncontaminated and without ISF. Since fluid from this region is transferred to the fluid receiving means and therefore needs to be accessible, this region is called the access region. This concept of transporting fluid from the capillary to the fluid receiving means serves to exclude disturbances of measurement by plasma or substances from the skin surface. It goes by its own that contamination by substances from the skin surface should be avoided if possible, in particular, when the amounts of sample for analysis are decreased to low amounts (e.g. below 1 microliter). For interstitial fluid it is known that this body fluid normally does not show the actual blood analyte concentrations but concentrations from 5 to 30 minutes before. This is due to the time delay of exchange between the blood compartment and the interstitial fluid compartment.

It has to be understood that this concept which avoids to contact the fluid receiving means with (contaminated) fluid received first in the channel can be applied to a number of device designs and is not restricted to sampling devices having a skin piercing element. This invokes a method of sampling fluid comprising the steps of
introducing fluid into an introduction region of a support structure which has a channel therein, said fluid filling an access region of the support structure which is accessible from the surrounding and the channel having a discharge region located downstream the access region
contacting a fluid receiving means with fluid located in the access region to receive fluid but not contacting it with fluid in the discharge region.

Figure 1C:
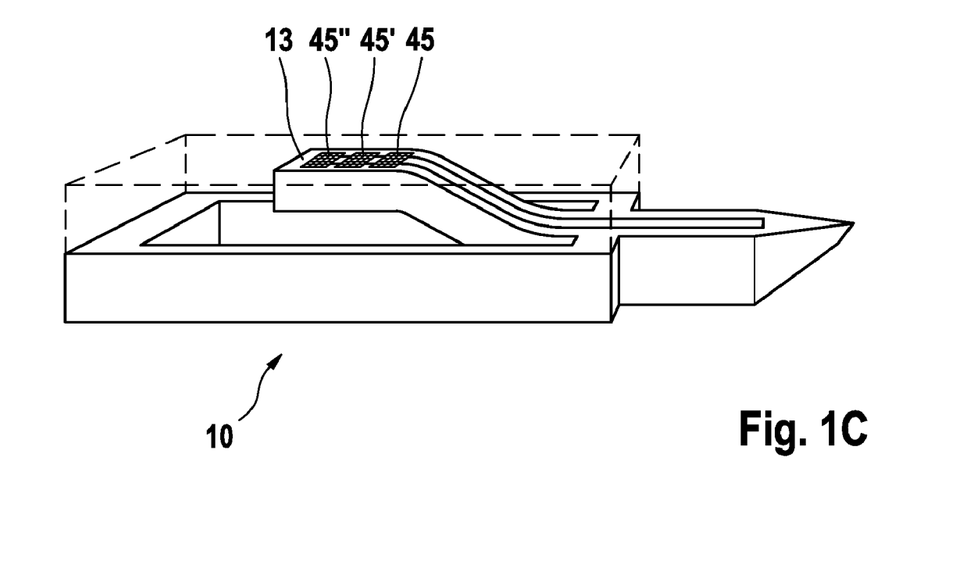
FIG. 1C shows the FIG. 1B embodiment with the moveable portion in contact with the test zone in a perspective view.

But now back to the embodiment shown in FIG. 1 where the support structure is a skin piercing element. The contacting between the moveable portion (13) and the test zones (45, 45', 45") can be seen in FIG. 1C. As this figure shows, the moveable portion due to its shape in form of a tongue can be bent upwardly. Based on the very thin structure of the skin piercing element the moveable section automatically will have enough flexibility if the skin piercing element is made from a ductile material. Suitable materials are e.g. metals, silicon and even ceramics which do not brake upon bending.

It has to be considered, that instead of bringing the capillary to the test zones it is also possible to bring the test zones to the capillary by e.g. bending the carrier.

Figure 2A:
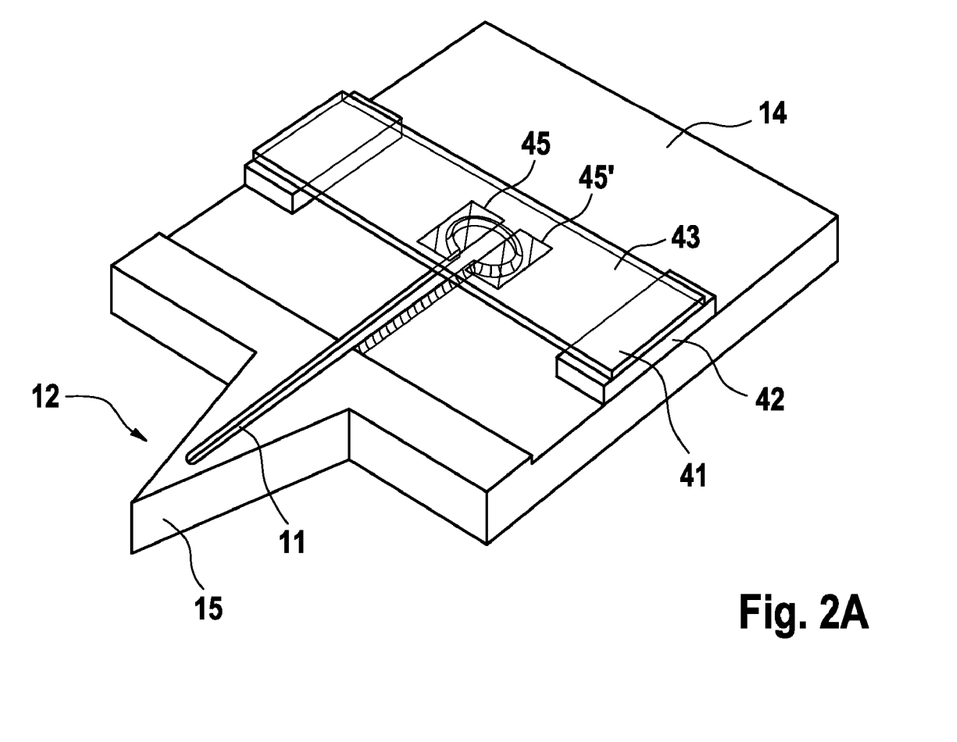
FIG. 2A shows a further embodiment with a moveable fluid receiving means.

FIG. 2 A shows a second embodiment where contact between the fluid channel and the fluid receiving means is accomplished by a moveable fluid receiving means. As in the first embodiment the skin piercing element has a protruding portion (12) with a tip (15) for piercing the skin. A fluid channel (11) in form of a capillary channel starts close to the piercing tip (15) and extends into an intermediate section of the holder portion (14). The fluid receiving means comprises a spacer (42) and a moveable carrier (43) fixed to the spacer. The moveable carrier (43) at its underside holds two test zones (45, 45') in form of a reagent matrix for optical detection. When the capillary channel (11) is filled with sample fluid the moveable carrier (43) is depressed and the test zones (45, 45') contacts the filled channel and take up body fluid. The transparent carrier (43) now can be illuminated and radiation reflected by the back side of the test zones (45, 45') can be measured to obtain a signal.

Figure 2B:
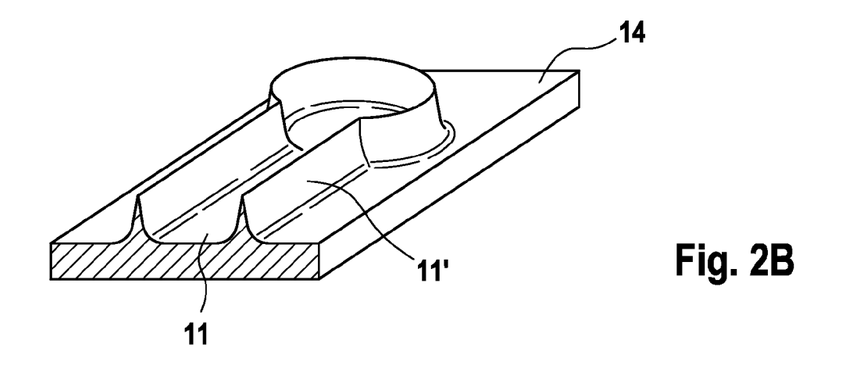
FIG. 2B shows a portion of the fluid channel from the FIG. 2A embodiment.
Figure 2C:
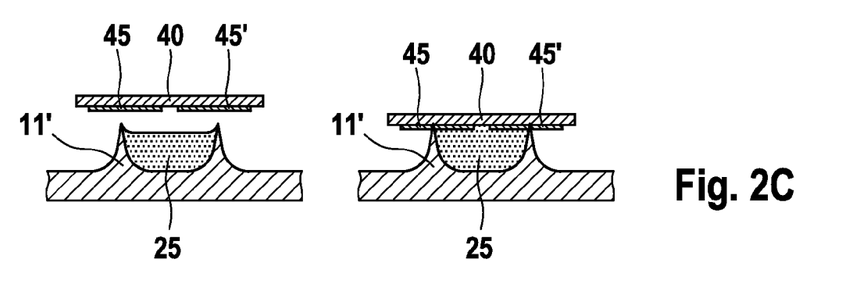
FIG. 2C shows the test zones near or in contact with the fluid pathway of the FIG. 2A embodiment.

FIG. 2 B shows the portion of the fluid channel (11) which contacts the sensors (45, 45') in more detail. As can be seen the channel has upstanding walls which protrude from the upper surface of the skin piercing element (14). The upstanding walls (11') have pointed edges. The function of these edges can better be seen in FIG. 2C which shows the interaction between a test zone and the fluid pathway (11). The left drawing of FIG. 2 C shows the test zones (45, 45') approaching the fluid pathway. The test zones (45, 45') are located at the underside of a carrier (40). The body fluid (25) residing in the fluid pathway (11) has a depressed conus. This means that a slight contact between the test zones and the walls of the fluid pathway may not be sufficient to contact the body fluid with the testing material. In the right hand drawing the function of the pointed edges can be seen which serves to depress the sensor material or even to cut it. Due to this the test zones on one hand are approaching the surface of body fluid more closely and on the other hand an intimate contact between the testing material and the channel walls is achieved. Both aspects improve transfer of body fluid from the fluid pathway onto the test zone.

FIG. 3 depicts four embodiments showing cuts through piercing elements and test zones. This will illustrate a technical problem which has to be accounted for. In FIG. 3a an embodiment is shown where a hydrophobic coating (16) has been applied on the body piercing element beside the fluid channel. As can be seen in FIG. 3a contact of the test zones with the skin piercing element does not only bring the test zones and body fluid into contact but during the contact capillary spaces are generated between the test zones (or the carrier) on one hand and the portions beside the fluid pathway on the other hand. This normally creates a high capillarity which transfers sample fluid residing in the channel not only on the test zones but also into the small capillary spaces which are generated. The hydrophobic coating (16) avoids sample fluid from creeping between the upper surface of the skin piercing element (14) and the carrier or test zones. It is desired to transfer the sample onto a dedicated area of the testing material so that the transferred amounts of sample fluid are sufficient to wet the test zones in a way that an accurate measurement can be achieved. Loosing sample fluid to other regions of the test zones or to the carrier could mean that the testing materials are not wetted sufficiently in the dedicated regions and measurement cannot be conducted properly.

Figure 3A:
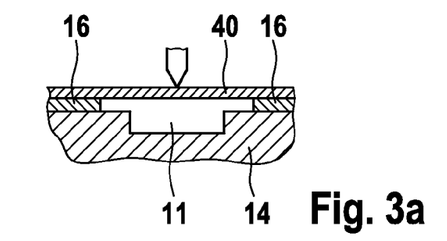
FIG. 3A shows a cross-sectional view of a further embodiment of a piercing element, a test zone, and a hydrophobic coating.
Figure 3B:
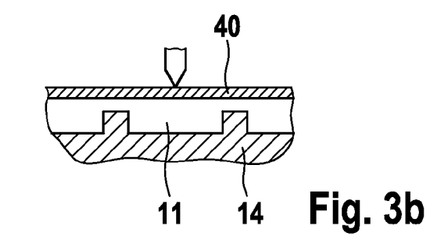
FIG. 3B shows a cross-sectional view of another embodiment of a piercing element and test zones.
Figure 3C:
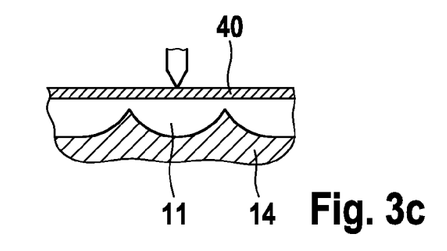
FIG. 3C shows a cross-sectional view of a third embodiment of a piercing element and test zones.
Figure 3D:
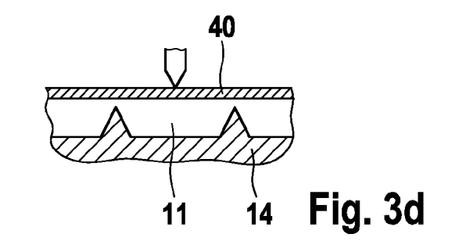
FIG. 3D shows a cross-sectional view of a fourth embodiment of a piercing element and test zones.

FIG. 3b shows a further embodiment which avoids an unintentional creeping of sample fluid. Similarly to FIG. 2 this embodiment has upstanding channel walls which contact the test zones or the carrier. Due to this, fluid that creeps into spaces stops at the outer channel walls and a loss of sample fluid is largely reduced. The channel walls, however, do not need to be square shaped as depicted in FIG. 3b but they may also be pointed as shown in FIG. 3c or 3d.

Figure 4A:
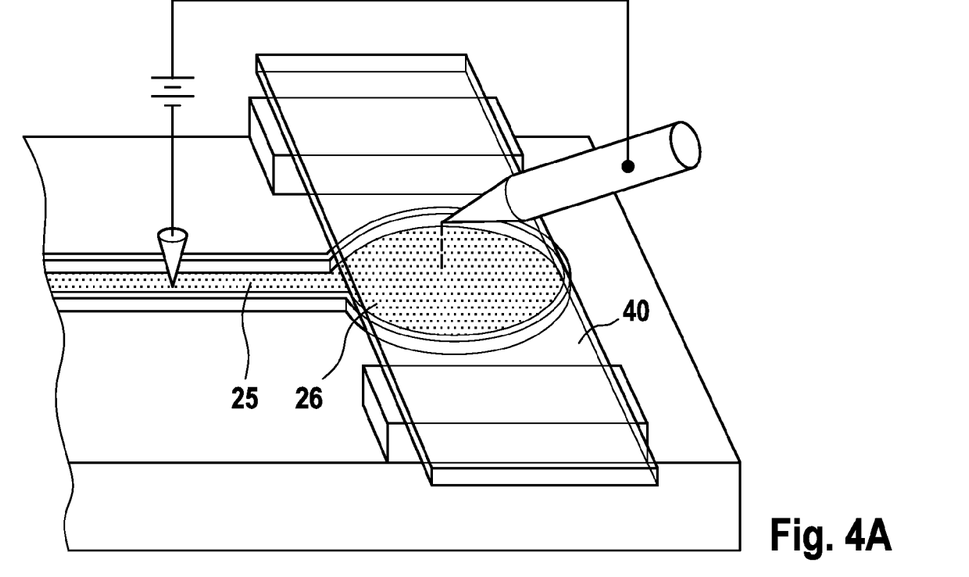
FIG. 4A illustrates the concept of electrical triggering a contact of sample fluid.

FIG. 4 shows the concept of electrical triggering a contact of sample fluid with the test zones. This general concept, however, is shown in FIG. 4 with respect to a skin piercing element as special embodiment of a support structure having a channel. For fluid triggering a high potential is applied between the sample fluid (25) and the carrier (40). This may cause either sample fluid to move from the channel onto the test zones or may cause a movement of the carrier in direction of the channel. In both cases wetting of the test zones by sample fluid can be triggered in a very short time frame by turning on the electrical potential. As can be seen by transparent drawing of the carrier the channel beneath the test zones leads into a collecting zone (26) for providing a larger amount of fluid for wetting the test zones than the thin capillary channel would provide.

Figure 4B:
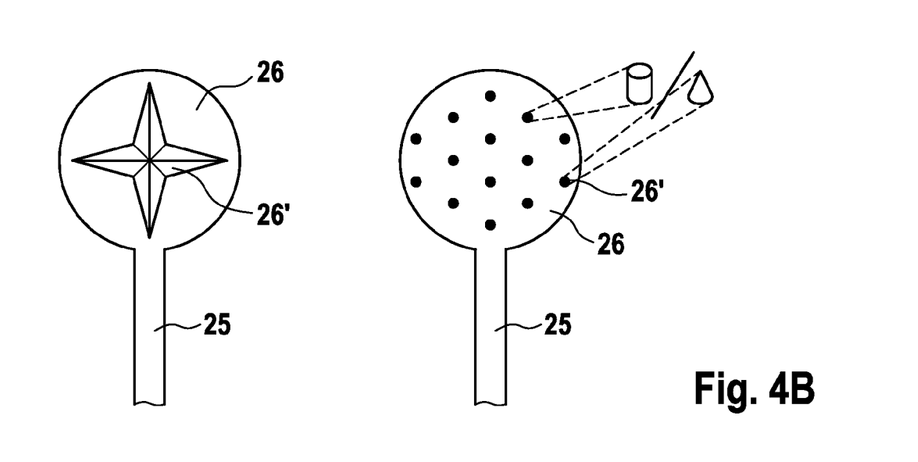
FIG. 4B shows two embodiments of collecting zones.

FIG. 4B depicts preferred embodiments of collecting zones in more detail. As can be seen the collecting zone (26) preferably has upstanding elements (26') which facilitate movement of fluid onto the test zones. These upstanding elements on one hand provoke high electrical charges at their end for transporting fluid and on the other hand they improve capillarity of the collecting zone (26) which improves filling with fluid.

Figure 5A:
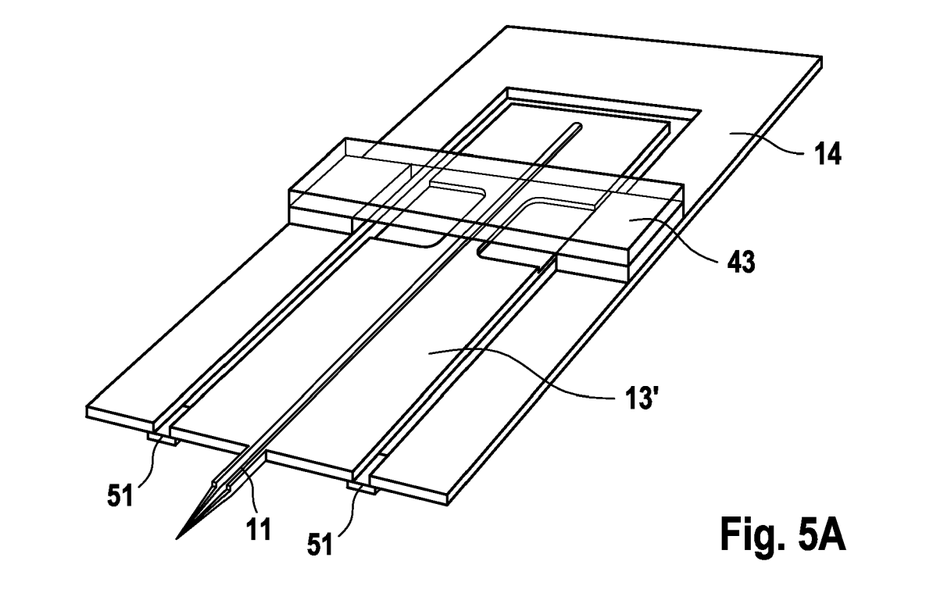
FIG. 5A depicts a design for providing a skin piercing element and a test zone in spaced apart geometry.

FIGS. 5A, B and C depict sampler designs for providing skin piercing element and test zones in a spaced apart geometry that allows contacting of test zones with sample fluid in the channel by actuation. The embodiment of FIG. 5A is similar to FIG. 1. The skin piercing element comprises a frame which is connected to an inner portion (13') in which runs the capillary channel (11). Inner portion and frame are connected by bendable portions (51). After filling of the capillary channel the inner portion is torsioned against the frame so that a portion of the capillary contacts the test zones beneath the carrier (43). By bending around the bendable portions the inner portion contacts the test zones in an angled manner. This has proven to be particularly advantageous since it provides a uniform wetting of the test zones without inclusion of air bubbles.

Figure 5B:
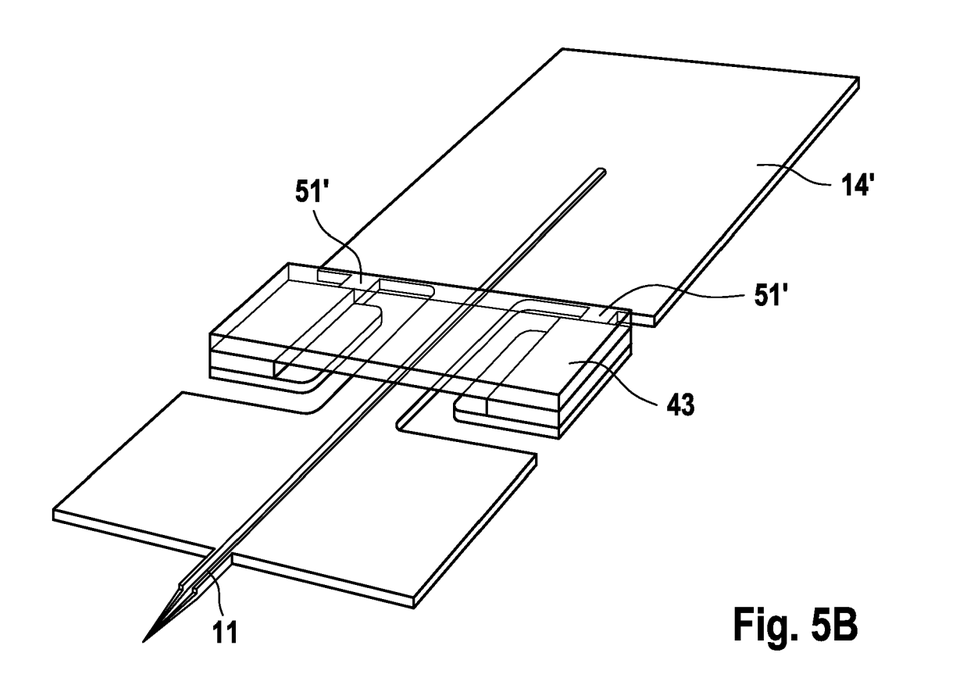
FIG. 5B depicts another embodiment of a design for providing a skin piercing element and a test zone in spaced apart geometry.

FIG. 5B shows an embodiment where the carrier (43) and its support are connected via bendable portions (51') to a main portion (14') which comprises the capillary. Again contact between capillary and test zones is accomplished in a tilted manner.

Figure 5C:
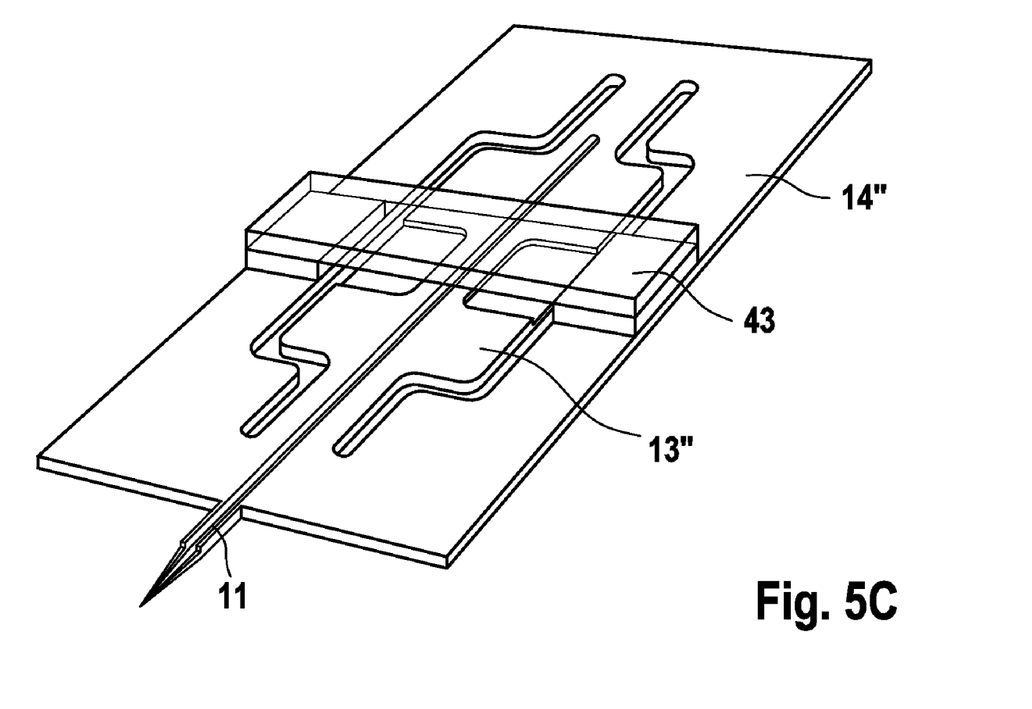
FIG. 5C depicts yet another embodiment of a design for providing a skin piercing element and a test zone in spaced apart geometry.

FIG. 5C shows an embodiment having an inner portion (13") which is connected at two ends to the frame portion (14"). When pressure is applied from the underside to the central part of the inner portion (13") this bends against the test zones beneath the carrier (43). By bowing this inner portion again an angled contacting is achieved.

Figure 6:
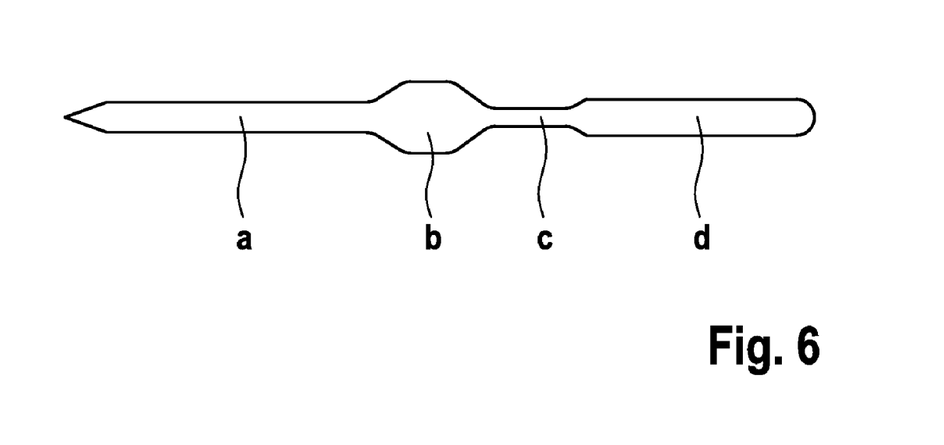
FIG. 6 schematically shows an improved shape of the capillary channel.

FIG. 6 schematically depicts an improved shape of the capillary channel. It has been found that the fill level of fluid in the channel generally increases with decreasing width of the capillary. The capillary of FIG. 6 has a first region (a) which leads into the tip portion of the skin piercing element. A second region (b) of increased diameter is for providing an increased sample volume. Particularly useful is third region (c) of decreased width. Due to the decreased width the fill level is increased and therefore transfer of fluid from the channel to the test zones has a high success rate. Therefore it is preferred to contact the test zones with the capillary in a tilted manner so that it first contacts region (c) and thereafter region (b). This ensures that fluid transfer will be initiated safely by region (c) and enough sample for testing is provided by region (b). Region (d) downstream region (c) may be employed to discharge contaminated sample fluid or ISF.

Figure 7A:
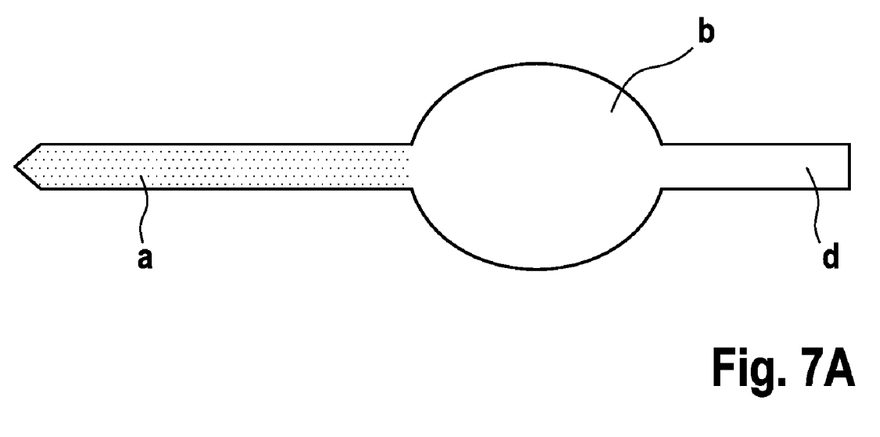
FIG. 7A shows a skin piercing element having regions with different cross section in a first configuration after skin has been pierced.
Figure 7B:
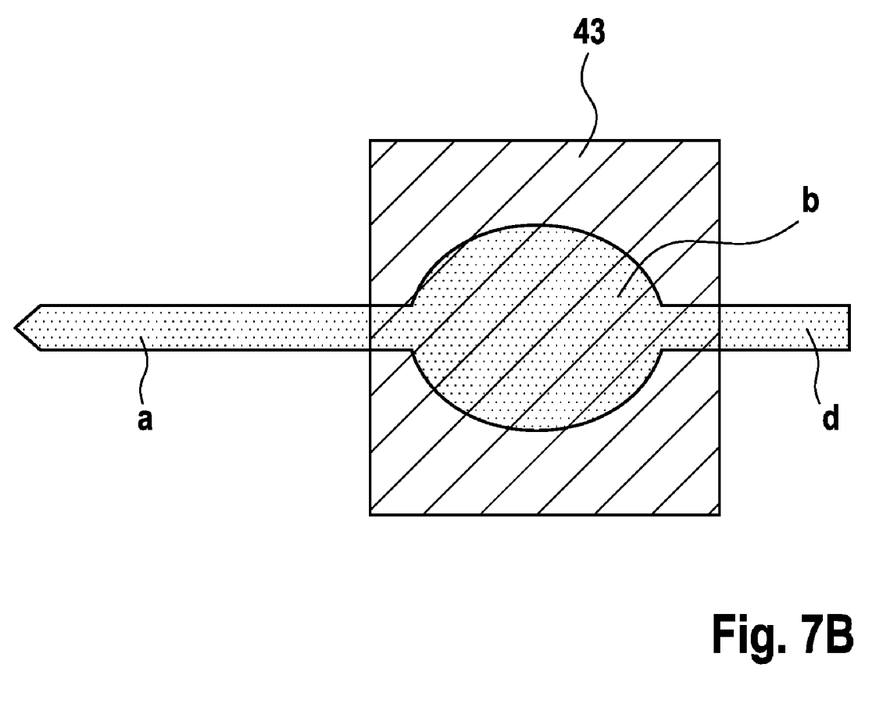
FIG. 7B shows the FIG. 7A embodiment in a second configuration after the skin piercing element is contacted with a carrier.

FIG. 7 shows a skin piercing element having a first region (a) leading into the tip region and a second region (b) of increased diameter. Picture A shows a status after skin has been pierced and blood was taken into region (a) of the capillary channel. Due to lower decreased capillarity of region (b) sample liquid fills region (a) but not region (b). When the skin piercing element is contacted with a carrier (43) the open channel structure (a, b, d) in some portion is closed at its top and capillarity is hence increased in this portion so that collection region (b) is filled and test zones on the underside of the carrier (43) come into contact with sample fluid. It is advantageous to have a circular detection area with view to the geometry of optical elements.

A skin piercing element according to FIG. 7 may be used in following method:
piercing skin
sampling body fluid into a portion of the capillary channel (region (a)).
contacting the capillary channel in a collecting region (b) with test zones and/or a carrier so that region (b) fills with body fluid
detecting changes of the test zones due to reaction with analyte from the body fluid.

Figure 8A:
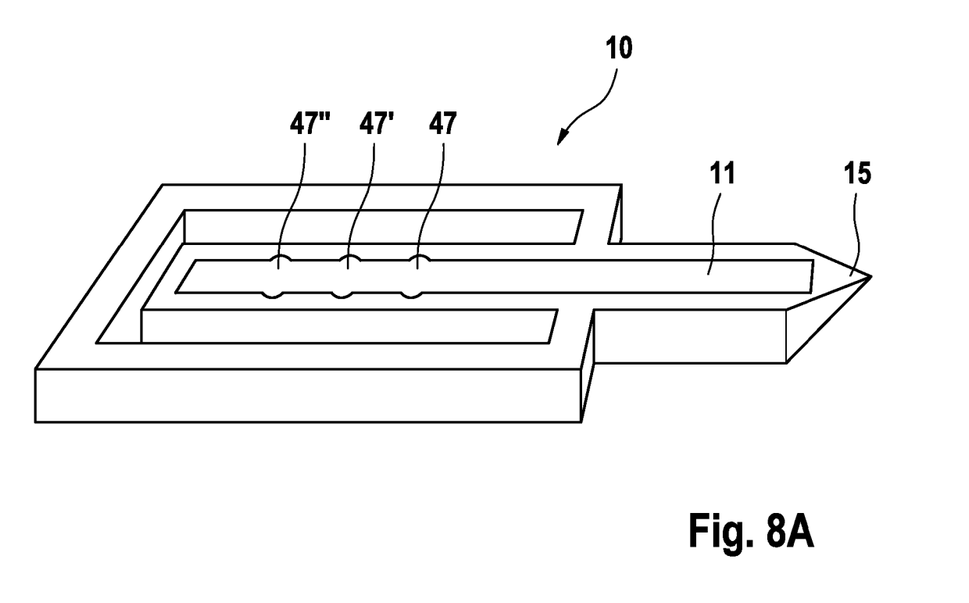
FIG. 8A shows a first embodiment of a skin piercing element which is adapted to provide sample fluid to multiple test zones.
Figure 8B:
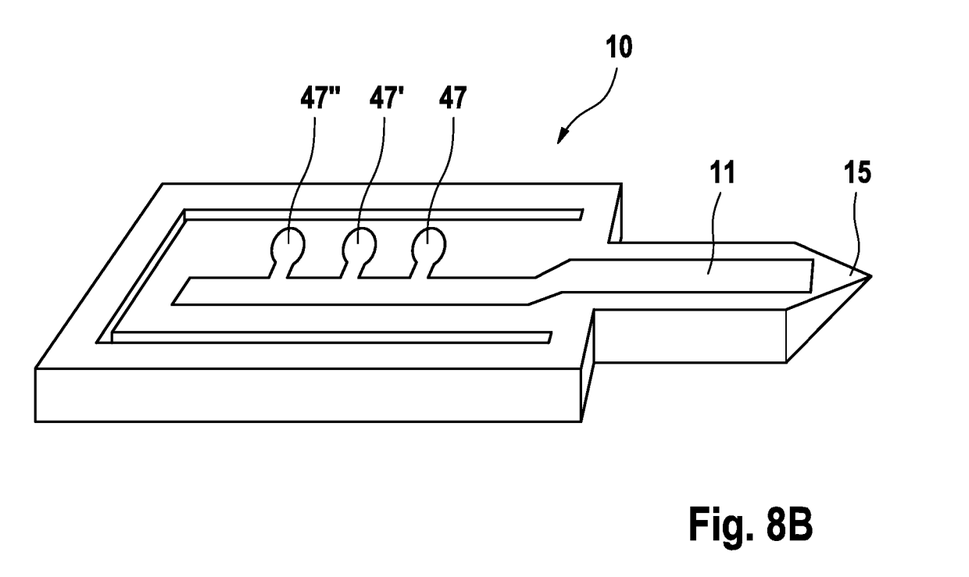
FIG. 8B shows a second embodiment of a skin piercing element which is adapted to provide sample fluid to multiple test zones.

FIGS. 8A und 8B show embodiments of skin piercing elements (10) which are adapted to provide sample fluid to multiple (three in the depicted cases) test zones. The fluid pathways (11) in both figures start in the front end region near to the sharpened tip (15). For further description of FIGS. 8A and 8B reference is made to FIG. 1. FIGS. 8A and 8B have reservoir zones (47, 47', 47") which serve to hold sample for wetting corresponding test zones when contacted with them. The reservoirs preferably have a larger diameter than the capillary channel (11) so that a larger amount of fluid is stored. In FIG. 8A the reservoir zones are integrated into the straight fluid pathway (11) while in FIG. 8B side channels branching off from the main fluid pathway are provided which lead fluid into the reservoir zones. Sampling elements of the present invention therefore may have side fluid channels which branch from the main fluid pathway and reservoirs provided in these side fluid channels. According to this the reservoir zones and hence the contact sites with test zones can be separated spatially to avoid interferences between the contact sites.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

What is claimed is:

1. A testing device comprising
a sampling element having a fluid pathway for receiving a sample fluid, the fluid pathway having an access region and an end portion, the end portion being downstream from the access region, wherein at least a portion of said fluid pathway is open to the environment and
a fluid receiving means being out of fluidic communication with said fluid pathway so that fluid in said pathway cannot contact the fluid receiving means initially wherein the fluid receiving means comprises two or more test zones and
wherein the two or more test zones are adapted to contact and fluidically communicate with the access region of the fluid pathway so that a fluid bolus entering the fluid pathway first and residing in the end portion of the fluid pathway is not contacted with the test zones.

2. Device according to claim 1, wherein the sampling element is a skin piercing element.

3. Device according to claim 1, wherein said device being adapted to undergo a physical change upon actuation so as to assume a contacting state in which a fluid in said fluid pathway contacts said fluid receiving means.

4. Device according to claim 3, wherein said device having a moveable portion which can be moved and at least a portion of said fluid pathway is located on said moveable portion.

5. Device according to claim 3, wherein said sampling element has a fluid transfer region and at least a portion of said fluid pathway in said fluid transfer region has pointed walls.

6. Device according to claim 5, wherein said fluid receiving means comprises a layer structure that can be depressed or cut by said pointed walls.

7. Device according to claim 1, wherein body fluid received in said fluid pathway is moved by electrical actuation onto the fluid receiving means.

8. Device according to claim 7, wherein the sampling element has a collection zone in which upstanding elements are located.

9. Device according to claim 1, wherein said sampling element or the fluid receiving means have confining means for confining the area of fluid transfer from the fluid pathway onto the fluid receiving means.

10. Device according to claim 9, wherein said fluid pathway has protruding wall portions and a surface adjacent to the fluid pathway is recessed with respect to the protruding wall portions.

11. Device according to claim 9, wherein a surface adjacent to the fluid pathway is hydrophobic.

12. Device according to claim 1, wherein said fluid receiving means comprises at least one of a reaction zone, a filtration zone and a mixing zone.

13. Device according to claim 1, wherein said sampling element has two or more fluid pathways.

14. Device according to claim 1, wherein said fluid pathway in a first region (a) has a first width and in another region (c) has a second width which is smaller than the first width.

15. Device according to claim 14, wherein said fluid pathway further comprises a collecting zone (b).

16. Device according to claim 1, wherein the two or more test zones are adapted to contact an intermediate section of the fluid pathway so that a fluid bolus entering the fluid pathway first and residing in the end portion of the fluid pathway is not contacted with the test zones.

17. Device according to claim 1, wherein the two or more test zones are adapted to simultaneously contact a fluid in said fluid pathway.

18. Device according to claim 1, wherein the two or more test zones are adapted to contact a fluid in said fluid pathway in a tilted manner.

19. System for body fluid analysis comprising
a sampling element with a fluid pathway for receiving body fluid and a skin piercing tip, the fluid pathway extending from the skin piercing tip to an end portion and including an access region upstream of the end portion, wherein at least a portion of said fluid pathway is open to the environment and a fluid receiving means being fluidically isolated from said fluid pathway during filling, there being no path for fluid to move between the fluid receiving means and the fluid pathway initially said fluid receiving means comprising two or more test zones adapted to contact and fluidically communicate with the access region of the fluid pathway and to avoid contact with the fluid first entering the fluid pathway.

20. System according to claim 19, wherein said system comprises a meter with a detection unit for receiving signals from at least one of said test zones to determine the presence and/or concentration of an analyte.

21. System according to claim 20, wherein said meter includes a holder in which said fluid receiving means is received and signal transmission from said at least one test zone to the detector is enabled.

22. System according to claim 20, wherein said meter has a processing unit that receives a signal indicating that the contacting means has contacted the fluid pathway with the fluid receiving means or that sample fluid has reached a test zone.

23. System according to claim 19, comprising a contacting means which contacts a portion of the fluid pathway of the sampling element with the fluid receiving means to provide at least one of said the test zones with sample fluid.

24. System according to claim 23, wherein said contacting means comprises voltage means for applying an electrical potential between said fluid pathway and said fluid receiving means so that fluid from said fluid pathway contacts fluid receiving means.

25. System according to claim 23, wherein said sampling element has a moveable portion and said contacting means applies a force to said moveable portion to move at least a portion of the fluid pathway into contact with the fluid receiving means.

26. System according to claim 19, wherein said sampling element is a skin piercing means and the system further comprising a drive means for driving the skin piercing means into skin to pierce the skin for obtaining a body fluid sample.

27. System according to claim 19, wherein the two or more test zones are adapted to simultaneously contact a fluid in said fluid pathway.

28. System according to claim 19, wherein the two or more test zones are adapted to contact a fluid in said fluid pathway in a tilted manner.

29. Analytical device comprising
a support structure having a channel therein which is accessible from the surrounding in at least an access region, said channel having a fluid introduction region as well as a discharge region located downstream the access region
a fluid receiving means, the fluid receiving means being out of fluidic communication with the channel in a first status and the fluid receiving means being in fluidic communication with the access region of the channel in a second status to receive fluid, so that the fluid receiving means is not contacted with a fluid from the discharge region,
wherein the fluid receiving means comprises two or more test zones.

30. Device according to claim 29, wherein the two or most test zones are adapted to simultaneously contact a fluid located in the access region.

31. Device of claim 29, wherein the two or more test zones are adapted to contact fluid located in the access region in a tilted manner.

32. Analytical device comprising
a support structure having a channel for receiving fluid therein which is accessible from the surrounding in at least an access region,
a fluid receiving means initially being fluidically isolated from the channel and comprising two or more test zones, there being no path for fluid to be initially transported from said channel to said fluid receiving means, and
a source of electrical potential which when turned on applies an electrical potential between fluid in said access region and said fluid receiving means so that fluid from said access region is transported simultaneously onto said two or more test zones.

33. Device according to claim 32, wherein the channel has a discharge region located downstream from the access region, and wherein fluid in the discharge region is not transported onto the two or more test zones.

* * * * *